United States Patent [19]

Schmerling

[11] 4,005,152
[45] Jan. 25, 1977

[54] CYCLOALKENYNES AND A METHOD FOR THE PREPARATION THEREOF

[75] Inventor: Louis Schmerling, Riverside, Ill.

[73] Assignee: Universal Oil Products Company, Des Plaines, Ill.

[22] Filed: Apr. 21, 1975

[21] Appl. No.: 569,899

Related U.S. Application Data

[63] Continuation-in-part of Ser. No. 428,635, Dec. 26, 1973, abandoned, which is a continuation-in-part of Ser. No. 196,792, Nov. 8, 1971, Pat. No. 3,799,997.

[52] U.S. Cl. .......................................... 260/648 R
[51] Int. Cl.$^2$ ................... C07C 23/08; C07C 23/10; C07C 23/14
[58] Field of Search ......... 260/648 R, 677 XA, 678

[56] References Cited
UNITED STATES PATENTS 2,561,516   7/1951   Ladd et al. .................... 260/654 D

OTHER PUBLICATIONS

Raphael, Acetylenic Compounds in Organic Synthesis, pp. 8–11 (1955).
Brandsma, Preparative Acetylenic Chemistry, pp. 103–105 (1971).
Johnson, The Chemistry of the Acetylenic Compounds, vol. II, pp. 3–14 (1950).

*Primary Examiner*—D. Horwitz
*Attorney, Agent, or Firm*—James R. Hoatson, Jr.; Raymond H. Nelson; William H. Page, II

[57] ABSTRACT

Cycloalkenic compounds containing a side-chain which possesses a halogenated acetylenic linkage may be prepared by dehydrochlorinating a cycloalkenic compound containing a chloro-substituted unsaturated substituent.

6 Claims, No Drawings

CYCLOALKENYNES AND A METHOD FOR THE PREPARATION THEREOF

CROSS-REFERENCE TO RELATED APPLICATIONS

This application is a continuation-in-part of my copending application Ser. No. 428,635 filed Dec. 26, 1973 now abandoned which is a continuation-in-part of application Ser. No. 196,792 filed Nov. 8, 1971 and now U.S. Pat. No. 3,799,997 issued Mar. 26, 1974, all teachings of which are incorporated herein by reference thereto.

BACKGROUND OF THE INVENTION

It is known in the prior art to dehydrochlorinate dichloroparaffins or chloroolefins in which the chlorine is attached to the double bond of the olefinic linkage for the purpose of preparing an acetylenic compound. However, the prior art has also taught that chloroacetylene in which the chlorine atom is attached to an acetylenic carbon atom is an extremely unstable compound and will explode unless it is diluted with hydrogen or nitrogen. It is also known in the prior art that it is possible to obtain an acetylenic compound in which one of the acetylenic carbons is attached to a carboxylic group and the other is attached to an aromatic ring, the triple bond being conjugated with the double bond or an aromatic ring but not an olefinic double bond. This prior art reference teaches the preparation of alkynes with a halogen attached to one of the triply-bonded carbon atoms, all of these compounds being halogen derivatives of propargylic acid. In contradistinction to this, the compounds of the present invention, as will hereinafter be shown in greater detail, will comprise cycloalkenynes in which the substituent comprising the side-chain on the cycloalkene may or may not be conjugated with the double bond of the cycloalkene ring. Furthermore, it was totally unexpected and surprising to discover that chloro-substituted acetylenes in which the acetylene was attached to a group containing a double bond are quite stable.

This invention relates to a process for the preparation of cycloalkenynes. More specifically the invention is concerned with a process for preparing cycloalkenic compounds containing a side-chain which possesses a halogenated acetylenic linkage, said acetylenic linkage being conjugated or non-conjugated with regard to the double bond in the cycloalkenic ring.

The products which are obtained by the process of the present invention which is hereinafter described in greater detail are useful compounds in the chemical field. For example, the chlorinated cycloalkenic compounds containing a side-chain which possesses an acetylene linkage in which the chlorine is attached to an acetylenic carbon atom such as 1-chloro-2-(1-cyclohexenyl)acetylene are useful in preparing flame retardant plastics and rubber when admixed with polymers such as polypropylene or rubbers such as Buna S. Inasmuch as the use of synthetic materials such as plastics is increasing to a great extent in the modern world, it is necessary that the synthetic materials possess certain desirable physical characteristics such as fire resistance, or flame retardancy, when utilized in certain instances where an exposure to the possibility of flame is present. Examples of places which may be subjected to excessive heat or to the action of a flame will include architectural panels for construction work, wall plugs for electrical connections, soundproofing material in walls, ceilings, etc., cable and wire coatings, appliance housings, underhood automotive use, heater ducts, TV cabinets, car or airplane interior components, automotive seats, boat interiors or exteriors, cushions for various vehicle seats such as airplane or automobile or bus seats, paint, lacquer, varnishes, protective films, etc.

It is therefore an object of this invention to provide a process for preparing compounds which contain both an ethylenic linkage and an acetylenic linkage.

A further object of this invention is to provide a process for the preparation of a cycloalkenic compound containing a halogenated acetylenic side-chain by dehydrochlorinating certain compounds of a type hereinafter set forth in greater detail.

In one aspect an embodiment of this invention resides in a process for the preparation of a cycloalkenic compound containing a sidechain which possesses a haloacetylenic linkage which comprises dehydrochlorinating a substituted cycloalkenic compound having the generic formula:

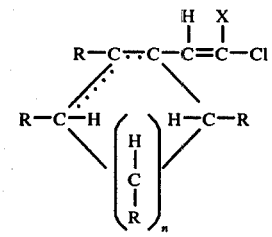

in which R is independently selected from the group consisting of hydrogen and lower alkyl radicals, X is selected from the group consisting of chlorine and bromine radicals and $n$ is an integer of from 1 to 3, the $C\doteq C\doteq C$ denoting a double-bond between the middle carbon atom and either of the other two carbon atoms and a single bond between the middle carbon atom and the remaining carbon atom, by treating said compound at an elevated temperature with an alkaline compound selected from the group consisting of alkali metal and alkaline earth metal hydroxides and carbonates dissolved in an alcohol containing from 1 to about 5 carbon atoms, and recovering the resultant cycloalkenic compound containing a side-chain which possesses a haloacetylenic linkage.

A further embodiment of this invention resides in a compound possessing the generic formula:

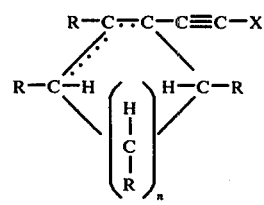

in which R is independently selected from the group consisting of hydrogen and lower alkyl radicals, X is selected from the group consisting of chlorine and bromine radicals and $n$ is an integer of from 1 to 3, the $C\doteq C\doteq C$ denoting a double-bond between the middle carbon atom and either of the other two carbon atoms and a single bond between the middle carbon atom and the remaining carbon atom.

A specific embodiment of this invention is found in a process for the preparation of a cycloalkenic compound containing a side-chain which possesses a haloacetylenic linkage which comprises dehydrochlorinating 1-(2,2-dichlorovinyl)-1-cyclohexene by treating said cyclohexene with an ethyl alcohol solution of potassium hydroxide at the reflux temperature of said solution and recovering the resultant 1-chloro-2-(1-cyclohexenyl)acetylene.

Another specific embodiment of this invention is found in a compound comprising 1-chloro-2-(1-cyclopentenyl)acetylene.

Other objects and embodiments will be found in the following further detailed description of the present invention.

The present invention is concerned with novel compounds comprising cycloalkenic compounds containing a haloacetylenic side-chain and to a process for preparing these compounds, said process involving the dehydrochlorination of certain cycloalkenic compounds containing a chlorinated unsaturated side-chain. As hereinbefore set forth, it has unexpectedly been found that these compounds may be prepared in this manner inasmuch as the prior art has indicated that acetylenic hydrocarbons containing a chlorine attached to the acetylenic carbon atom linkage by replacing an acetylenic hydrogen atom is an unstable compound and will spontaneously explode unless diluted with hydrogen or nitrogen. Likewise, the prior art is also completely silent on cycloalkenyl acetylene compounds, either conjugated or non-conjugated in nature.

The starting materials for the novel compounds of the present invention may be obtained by the free-radical induced condensation of cycloolefins or bicycloolefins with trichloroethylenes. Trihaloethylenes are necessary reactants in order that the condensation product of the reaction between them and the cycloolefinic compound will result in the desired configuration necessary for the dehydrochlorination to prepare the desired product. Suitable trihaloethylenes which may be utilized to form the desired starting material will include trichloroethylene and 1-bromo-1,2-dichloroethylene.

Examples of cycloolefins and bicycloolefins which may be condensed with the aforementioned polychloroolefins will include cyclopentene, cyclohexene, cycloheptene, norbornene, 3-methyl-1-cyclopentene, 4-methyl-1-cyclopentene, 5-methyl-1-cyclopentene, 3,4-dimethyl-1-cyclopentene, 3,4,5-trimethyl-1-cyclopentene, 3-ethyl-1-cyclopentene, 4-ethyl-1-cyclopentene, 5-ethyl-1-cyclopentene, 3,4-diethyl-1-cyclopentene, 3,4,5-triethyl-1-cyclopentene, 3-propyl-1-cyclopentene, 4-propyl-1-cyclopentene, 5-propyl-1-cyclopentene, 3,4-dipropyl-1-cyclopentene, 3,4,5-tripropyl-1-cyclopentene, 3-butyl-1-cyclopentene, 4-butyl-1-cyclopentene, 5-butyl-1-cyclopentene, 3,4-dibutyl-1-cyclopentene, 3,4,5-tributyl-1-cyclopentene, 3-methyl-1-cyclohexene, 4-methyl-1-cyclohexene, 5-methyl-1-cyclohexene, 3,4-dimethyl-1-cyclohexene, 3,4,5-trimethyl-1-cyclohexene, 3-ethyl-1-cyclohexene, 4-ethyl-1-cyclohexene, 5-ethyl-1-cyclohexene, 3,4-diethyl-1-cyclohexene, 3,4,5-triethyl-1-cyclohexene, 3-propyl-1-cyclohexene, 4-propyl-1-cyclohexene, 5-propyl-1-cyclohexene, 3,4-dipropyl-1-cyclohexene, 3,4,5-tripropyl-1-cyclohexene, 3-methyl-1-cycloheptene, 4-ethyl-1-cycloheptene, 5-methyl-1-cycloheptene, 6-methyl-1-cycloheptene, 3,4-dimethyl-1-cycloheptene, 3,4,5-trimethyl-1-cycloheptene, 3,4,5,6-tetramethyl-1-cycloheptene, 3-ethyl-1-cycloheptene, 4-methyl-1-cycloheptene, 5-ethyl-1-cycloheptene, 6-ethyl-1-cycloheptene, 3,4-diethyl-1-cycloheptene, 3,4,5-triethyl-1-cycloheptene, 3,4,5,6-tetraethyl-1-cyclcoheptene, etc. It is to be understood that the aforementioned trihaloethylenes and cycloolefins are only representative of the class of starting materials and that the present invention is not necessarily limited thereto.

The condensation of the aforementioned cycloolefins and trihaloethylenes is effected in the presence of a catalyst which is capable of forming free radicals under the conditions at which the reaction is effected. These include peroxy compounds containing the bivalent radical, -O-O-, and which are capable of inducing the condensation of the cycloolefins with the polychloroolefins. The organic peroxy compounds constitute a preferred class of catalyst and include peracetic acid, persuccinic acid, dimethyl peroxide, diethyl peroxide, di-t-butyl peroxide, dipropyl peroxide, acetyl benzyl peroxide, acetyl peroxide, propionyl peroxide, butyryl peroxide, lauroyl peroxide, benzoyl peroxide, tetralin peroxide, urea peroxide, t-butyl perbenzoate, t-butyl hydroperoxide, etc. Other catalysts which may be used are the persulfates, perborates, and percarbonates of ammonium and the alkali metals, etc., as well as mixtures of the peroxy compounds. Only catalytic amounts, less than stoichiometric amount, need be used to effect the condensation.

The reaction temperature which is employed to effect the condensation should be at least as high as the initial decomposition temperature of the free-radical generating catalyst, such as a peroxide compound, in order to liberate and form free radicals which promote the reaction. However, the operating temperature generally does not exceed the decomposition temperature of the catalyst by more than about 150° C. In the continuous method of carrying out this process, the catalysts preferably are added intermittently, particularly when a packing material is used which retains the catalyst in the reaction zone. When a free-radical generating catalyst such as tert-butyl perbenzoate is used, having a decomposition temperature of approximately 115° C., the operating temperature of the process is from about 115° C. to about 265° C. When di-tert-butyl peroxide having a decomposition temperature of about 130° C. is used, the process is run at a temperature of from about. 130° C. to about 280° C. A temperature below 130° C. may be used, but the reaction time will need to be very long. Higher reaction temperatures may be employed, but little advantage is gained if the temperature is more than the hereinbefore mentioned 150° C. higher than the decomposition temperature of the catalyst. The general effect of increasing the operating temperature is to accelerate the rate of the condensation reaction between the polyhaloolefins and the ether. However, the increased rate of reaction is accompanied by certain amounts of decomposition. The preferred operating pressure of the process is that needed to keep a substantial portion of the reactants in a liquid phase and will generally range from atmospheric pressure to about 100 atmospheres or more.

Concentrations of the catalyst which are employed to effect the condensation of the cycloolefin and polychloroolefin may also vary over a rather wide range, but it is desirable to use low concentrations of catalysts such as from about 0.1% to about 10% of the total weight of the cycloolefin and the trihaloethylene. In addition, the reaction time which is required to effect the condensation of the two compounds may be within the range of slightly less than 1 minute to several hours in duration. However, contact times of at least 10 minutes are usually preferred.

The compounds which form the starting materials which result in the novel compounds of the present invention which are prepared according to the hereinbefore set forth process will include the generic formula:

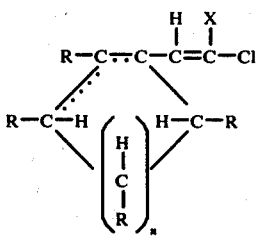

in which R is independently selected from the group consisting of hydrogen and lower alkyl radicals, X is independently selected from the group consisting of chlorine and bromine radicals and $n$ is an integer of from 1 to 3. Some representative examples of compounds possessing this formula will include 1-(2,2-dichlorovinyl)-1-cyclopentene, 1-(2,2-dichlorovinyl)-1-cyclohexene, 3-(2,2-dichlorovinyl)-1-cyclohexene, 1-(2,2-dichlorovinyl)-1-cycloheptene, 3-(2,2-dichlorovinyl)-1-cycloheptene, 1-(2,2-dichlorovinyl)-2-methyl-1-cyclopentene, 1-(2,2-dichlorovinyl)-2-methyl-1-cyclohexene, 1-(2,2-dichlorovinyl)-2-methyl-1-cycloheptene, 3-(2,2-dichlorovinyl)-2,3-dimethyl-1-cyclopentene, 3-(2,2-dichlorovinyl)-2,3-dimethyl-1-cyclohexene, 1-(2,2-dichlorovinyl)-2,3-dimethyl-1-cycloheptene, 1-(2-chloro-2-bromovinyl)-2,3-dimethyl-1-cyclopentene, 1-(2-chloro-2-bromovinyl)-2,3-dimethyl-1-cyclohexene, 1-(2-chloro-2-bromovinyl)-2,3-dimethyl-1-cycloheptene, 1-(2,2-dichlorovinyl)-2,3-diethyl-1-cyclopentene, 1-(2,2-dichlorovinyl)-2,3-diethyl-1-cyclohexene, 1-(2,2-dichlorovinyl)-2,3-diethyl-1-cycloheptene, 1-(2,2-dichlorovinyl)-2,3,4-trimethyl-1-cyclopentene, 1-(2,2-dichlorovinyl)-2,3,4-trimethyl-1-cyclohexene, 1-(2,2-dichlorovinyl)-2,3,4-trimethyl-1-cycloheptene, 1-(2-chloro-2-bromovinyl)-1-cyclopentene, 1-(2-chloro-2-bromovinyl)-1-cyclohexene, 1-(2-chloro-2-bromovinyl)-1-cycloheptene, 3-(2-chloro-2-bromovinyl)-2,3-dimethyl-1-cyclopentene, 3-(2-chloro-2-bromovinyl)-2,3-dimethyl-1-cyclohexene, 3-(2-chloro-2-bromovinyl)-2,3-dimethyl-1-cycloheptene, 1-(2-chloro-2-bromovinyl)-2,3-dipropyl-1-cyclopentene, 1-(2-chloro-2-bromovinyl)-2,3-dipropyl-1-cyclohexene, 1-(2-chloro-2-bromovinyl)-2,3-dipropyl-1-cycloheptene, 1-(2-chloro-2-bromovinyl)-3-butyl-1-cyclopentene, 1-(2-chloro-2-bromovinyl)-3-butyl-1-cyclohexene, 1-(2-chloro-2-bromovinyl)-3-butyl-1-cycloheptene, etc. It is to be understood that the aforementioned compounds are only representative of the class of compounds which may be used as starting materials in the dehydrochlorination reaction, and that the present invention is not necessarily limited thereto.

The aforementioned chloro-substituted compounds are dehydrochlorinated by treatment with an alcoholic solution of an alkaline compound at dehydrohalogenation conditions. Examples of alkaline compounds will include compounds containing an alkali metal or an alkaline earth metal such as lithium hydroxide, potassium hydroxide, sodium hydroxide, rubidium hydroxide, cesium hydroxide, calcium hydroxide, magnesium hydroxide, strontium hydroxide, lithium carbonate, sodium carbonate, potassium carbonate, rubidium carbonate, cesium carbonate, magnesium carbonate, strontium carbonate, etc. Of the aforementioned alkaline compounds, the preferred ones comprise potassium hydroxide and sodium hydroxide. Alkali metal alkoxides and alkaline earth alkoxides such as potassium butoxide may also be used but not necessarily with equivalent results. Examples of alcohols which contain from 1 to 5 carbon atoms and which may be used as a medium in which the dehydrochlorination is effected will include methyl alcohol, ethyl alcohol, n-propyl alcohol, isopropyl alcohol, n-butyl alcohol, sec-butyl alcohol, t-butyl alcohol, n-amyl alcohol, sec-amyl alcohol, t-amyl alcohol, etc., the preferred alcohols comprising methyl alcohol, ethyl alcohol and propyl alcohol due to their readily greater availability and lower boiling point. The dehydrochlorination reaction is effected at elevated temperatures ranging from about 65° up to about 150° C. or more, the preferred temperature being the refluxing temperature of the particular alcohol which is employed as the medium.

It is comtemplated within the scope of this invention that the dehydrochlorination reaction may be effected in any suitable manner and may comprise either a batch or continuous type operation. For example, when a batch type operation is used, a quantity of the chloro- or polychlorocycloolefin of the type hereinbefore set forth in greater detail is placed in an appropriate apparatus provided with heating and reflux means, the alcoholic solution containing the alkaline compound is added and the mixture is then heated to the desired operating temperature. Upon completion of the desired residence time which may range from about 0.5 up to about 10 hours or more in duration, the reaction mixture is recovered, the mixture is then subjected to conventional means of separation and purification including extraction, washing, drying, fractional distillation, etc., whereby the dehydrochlorinated product comprising a cycloalkenic compound containing an acetylenically substituted side-chain is recovered.

Another method of effecting the process of the present invention is by continuous manner of operation wherein the starting material is continuously charged to the reaction zone which is maintained at the proper operating conditions of temperature and pressure. The alcoholic solution containing the alkaline compound is also continuously charged to the reactor through a separate line or, if so desired, it may be admixed with the starting material and the resulting mixture charged to said reactor in a single stream. Upon completion of the desired residence time, the reactor effluent is continuously withdrawn and subjected to conventional means of separation of the type hereinbefore set forth whereby the desired cycloalkenic compound containing an acetylenically substituted side-chain is recovered while any unreacted starting material, alkaline compound and alcoholic solution are recycled to form a portion of the feed stock.

Some specific examples of the novel compositions of matter of the present invention which comprise cycloalkenic compounds containing a haloacetylenic side-chain which may be obtained from utilizing the process herein described will include compounds possessing the generic formula:

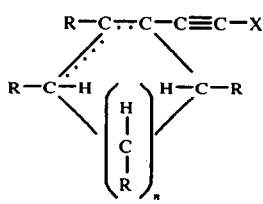

in which R is independently selected from the group consisting of hydrogen and lower alkyl radicals, X is selected from the group consisting of chlorine and bromine radicals and n is an integer of from 1 to 3. Such cycloalkenic compounds containing a side-chain which possesses a haloacetylenic linkage include 1-chloro-2-(1-cyclopentenyl)acetylene, 1-chloro-2-(1-cyclohexenyl)acetylene, 1-chloro-2-(1-cycloheptenyl)acetylene, 1-chloro-2-(2-cyclopentenyl)acetylene, 1-chloro-2-(2-cyclohexenyl)acetylene, 1-chloro-2-(2-cycloheptenyl)acetylene, 1-chloro-2-(1-methyl-1-cyclopentenyl)acetylene, 1-chloro-2-(2-methyl-1-cyclohexenyl)acetylene, 1-chloro-2-(1-methyl-1-cycloheptenyl)acetylene, 1-chloro-2-(2,3-dimethyl-1-cyclopentenyl)acetylene, 1-chloro-2-(2,3-dimethyl-1-cyclohexenyl)acetylene, 1-chloro-2-(2,3-dimethyl-1-cycloheptenyl)acetylene, 1-bromo-2-(1-cyclopentenyl)acetylene, 1-bromo-2-(1-cyclohexenyl)acetylene, 1-bromo-2-(1-cycloheptenyl)acetylene, 1-bromo-2-(3-butyl-1-cyclopentenyl)acetylene, 1-bromo-2-(3-butyl-1-cyclohexenyl)acetylene, 1-bromo-2-(3-butyl-1-cycloheptenyl)acetylene, 1-chloro-2-(2-cyclopentenyl)acetylene, 1-chloro-2-(2cyclohexenyl)acetylene, 1-chloro-2-(2-cycloheptenyl)acetylene, 1-chloro-2-(2-methyl-2-cyclopentenyl)acetylene, 1-chloro-2-(2-methyl-2-cyclohexenyl)acetylene, 1-chloro-2-(2-methyl-2-cycloheptenyl)acetylene, 1-chloro-2-(2,3-dimethyl-2-cyclopentenyl)acetylene, 1-chloro-2-(2,3-dimethyl-2-cyclohexenyl)acetylene, 1-chloro-2-(2,3-dimethyl-2-cycloheptenyl)acetylene, 1-bromo-2-(2-cyclohexenyl)acetylene, 1-bromo-2-(1-cycloheptenyl)acetylene, 1-bromo-2-(1-butyl-1-cyclopentenyl)acetylene, 1-bromo-2-(1-butyl-1-cyclohexenyl)acetylene, 1-bromo-2-(1-butyl-1-cycloheptenyl)acetylene, etc. It is to be understood that the aforementioned compounds are only representative of the type of cycloalkenic compounds containing an acetylenic side-chain which may be prepared according to the hereinbefore set forth process, and that the present invention is not necessarily limited thereto.

The following examples are given to illustrate the novel compounds of the present invention and also the processes which are employed to prepare the same. However, these examples are not intended to limit the generally broad scope of the present invention in strict accordance therewith.

EXAMPLE I

To a glass liner of a rotating autoclave is charged a mixture comprising 41 grams (0.6 mole) of cyclopentene, 136 grams (1.0 mole) of trichloroethylene and 6 grams (0.04 mole) of di-t-butyl peroxide. The autoclave is sealed and nitrogen is pressed in until an initial operating pressure of 30 atmospheres is reached. The autoclave is then heated to a temperature of 130° C. and maintained in a range of from about 130°–140° C. for a period of 4 hours, the maximum pressure at this temperature reaching approximately 50 atmospheres. At the end of the 4-hour period, heating is discontinued and the autoclave is allowed to return to room temperature, the final pressure at room temperature being 30 atmospheres. The excess pressure is discharged and the autoclave is opened. The reaction product is recovered and subjected to fractional distillation, the desired cut comprising 1-(2,2-dichlorovinyl)-1-cyclopentene being recovered therefrom.

The 1-(2,2-dichlorovinyl)-1-cyclopentene which is prepared according to the above paragraph is dehydrochlorinated by heating with an alcoholic alkaline solution comprising 8.3 grams of potassium hydroxide in 100 cc of a 95% ethyl alcohol solution for a period of 4 hours, the temperature of the reaction being the reflux temperature of the alcohol, i.e., about 78° C. The clear product is filtered from the potassium chloride which precipitates out, washed with water and extracted with ether. The washed ether extract is dried over potassium carbonate and distilled to remove the ether. The desired product comprising 1-chloro-2-(1-cyclopentenyl)acetylene is recovered.

EXAMPLE II

In this example a mixture comprising 50 grams (0.8 mole) of cyclohexene, 136 grams (1.0 mole) of trichloroethylene and 6 grams (0.04 mole) of di-t-butyl peroxide was placed in the glass liner of a rotating autoclave and treated in a similar manner to that hereinbefore set forth, that is, the autoclave was sealed, nitrogen pressed in until an initial operating pressure of 30 atmospheres was reached and thereafter the autoclave was heated to a temperature of 130° C. The autoclave and contents thereof were maintained in a range of from 130°–140° C. for a period of 4 hours, during which time the maximum pressure rose to 49 atmospheres. At the end of the 4-hour period, heating was discontinued, the autoclave was allowed to return to room temperature, the excess pressure of 30 atmospheres was discharged and the reaction product which comprised a dark amber liquid was recovered. The product was subjected to fractional distillation and the cut boiling at 70°–77° C. at 10.0 mm. pressure was recovered. This cut was analyzed with the following results:

Calculated for: $C_8H_{10}Cl_2$: C, 54.26%; H, 5.69%; Found: C, 54.27%; H, 5.78%.

This cut comprised 1-(2,2-dichlorovinyl)-1-cyclohexene and 3-(2,2-dichlorovinyl)-1-cyclohexene.

In like manner the aforementioned (2,2-dichlorovinyl)-1-cyclohexenes were heated at a reflux temperature of 78° C. with an ethyl alcohol solution of potassium hydroxide for a period of 4 hours during which time potassium chloride precipitated out. The precipitate was removed by filtration and the liquid product was subjected to purification means similar to those hereinbefore set forth, that is, by washing with water and extraction with ether. The washed ether extract was dried over potassium carbonate and distilled to remove the ether. The residue was submitted to analysis which disclosed the presence of 1-chloro-2-(1-cyclohexenyl)acetylene and 1-chloro-2-(2-cyclohexenyl)acetylene.

EXAMPLE III

In this example a mixture comprising 48 grams (0.5 mole) of cycloheptene, 105 grams (0.8 mole) of trichloroethylene and 6 grams (0.04 mole) of di-t-butyl peroxide is placed in the glass liner of a rotating autoclave which is thereafter sealed and nitrogen is pressed in until an initial operating pressure of 30 atmospheres is reached. The autoclave and contents thereof are treated in a manner similar to that hereinbefore set forth, that is, by heating to a temperature of 130° C. and maintaining the temperature in a range of from 130°-140° C. for a period of 4 hours. At the end of this time, heating is discontinued, the autoclave is allowed to return to room temperature and the excess pressure is discharged. The reaction product which comprises a dark amber liquid is recovered, subjected to fractional distillation and the desired cut comprising 1-(2,2-dichlorovinyl)cycloheptenes is separated and recovered.

The 1-(2,2-dichlorovinyl)cycloheptenes which are prepared according to the above paragraph are then heated at the reflux temperature of 78° C. with an ethyl alcohol solution of sodium hydroxide for a period of 6 hours, during which time the sodium chloride precipitates out. The precipitate is removed by filtration and the filtrate is subjected to purification means similar to those hereinbefore set forth whereby the washed ether extract comprising 1-chloro-2-(x-cycloheptenyl)acetylene (where x designates an undetermined position of the double bond) is recovered.

EXAMPLE IV

In like manner a mixture comprising 100 grams (1 mole) of 1-methyl-1-cyclohexene, 105 grams (0.8 mole) of trichloroethylene and 6 grams (0.04 mole) of di-t-butyl peroxide is placed in the glass liner of a rotating autoclave which is thereafter sealed and nitrogen is pressed in until an initial operating pressure of 30 atmospheres is reached. The autoclave is then heated to a temperature of 130° C. and maintained in a range of from about 130°-140° C. for a period of 4 hours, the maximum pressure during this residence time reaching about 50 atmospheres. At the end of the 4 hours, heating is discontinued, the autoclave is allowed to return to room temperature and the excess pressure is discharged. The autoclave is opened, the reaction product is recovered therefrom and thereafter subjected to fractional distillation, the cut comprising 1-(2,2-dichlorovinyl)-2-methyl-1-cyclohexene being recovered therefrom.

The substituted cyclohexene which is prepared according to the above paragraph is then subjected to a dehydrochlorination step in a manner similar to that set forth above by treating said compound with an ethyl alcohol solution of potassium hydroxide at a reflux temperature of about 78° C. for a period of 4 hours. The potassium chloride which precipitates out is filtered and the liquid product is subjected to washing with water, extraction with ether and drying over potassium carbonate, the desired product comprising 1-chloro-2-(2-methyl-1-cyclohexenyl)acetylene is recovered therefrom.

EXAMPLE V

In this example a mixture comprising 77 grams (0.8 mole) of 3-methyl-1-cyclohexene along with 132 grams (1.0 mole) of trichloroethylene and 6 grams (0.04 mole) of di-t-butyl peroxide is placed in the glass liner of a rotating autoclave. The autoclave and contents thereof are then treated in a manner similar to that set forth in the above examples. At the end of the 4-hour residence time, heating is discontinued, the autoclave is allowed to return to room temperature and the excess pressure is discharged. The reaction product which comprises a dark amber liquid is recovered and subjected to fractional distillation whereby the desired cut comprising 1-(2,2-dichlorovinyl)-3-methyl-1-cyclohexene and 3-(2,2-dichlorovinyl)-1-methyl-1-cyclohexene is recovered. This compound is then subjected to dehydrochlorination by treatment with an ethyl alcohol solution of potassium hydroxide at a temperature of about 78° C. for a period of 4 hours. The potassium chloride which precipitates is filtered and the liquid product is thereafter washed with water, extracted with ether, dried over potassium carbonate and distilled to remove the ether. The residue which comprises 1-chloro-2-(3-methyl-1-cyclohexenyl)acetylene and 1-chloro-2-(3-methyl-2-cyclohexenyl)acetylene is recovered.

I claim as my invention:

1. A compound possessing the generic formula:

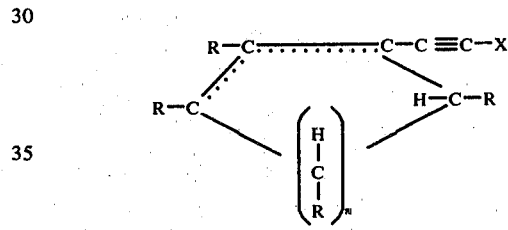

in which R is independently selected from the group consisting of hydrogen and lower alkyl radicals, X is selected from the group consisting of chlorine and bromine radicals and n is an integer from 1 to 3, and wherein C C C denotes a double bond between the middle carbon atom and either of the other two carbon atoms and a single bond between the middle carbon atom and the remaining carbon atom.

2. The compound of claim 1 being 1-chloro-2-(1-cyclohexenyl)acetylene.

3. The compound of claim 1 being 1-chloro-2-(1-cyclopentenyl)acetylene.

4. The compound of claim 1 being 1-chloro-2-(x-cycloheptenyl)acetylene wherein x designates an undetermined position of the double bond.

5. The compound of claim 1 being 1-chloro-2-(2-methyl-1-cyclohexenyl)acetylene.

6. The compound of claim 1 being a 1-chloro-2-(3-methylcyclohexenyl)acetylene.

* * * * *